(12) United States Patent
Egilsson et al.

(10) Patent No.: US 9,295,567 B2
(45) Date of Patent: *Mar. 29, 2016

(54) SUSPENSION LINER SYSTEM WITH SEAL

(71) Applicant: OSSUR hf, Reykjavik (IS)

(72) Inventors: Egill Sveinbjorn Egilsson, Reykjavik (IS); Sigurdur Asgeirsson, Gardabaer (IS)

(73) Assignee: OSSUR hf, Reykjavik (IS)

( * ) Notice: Subject to any disclaimer, the term of this patent is extended or adjusted under 35 U.S.C. 154(b) by 4 days.

This patent is subject to a terminal disclaimer.

(21) Appl. No.: 14/281,424

(22) Filed: May 19, 2014

(65) Prior Publication Data

US 2014/0257522 A1    Sep. 11, 2014

Related U.S. Application Data

(60) Continuation of application No. 13/765,127, filed on Feb. 12, 2013, now Pat. No. 9,056,022, which is a continuation of application No. 13/179,896, filed on Jul. 11, 2011, now Pat. No. 8,894,719, which is a (Continued)

(51) Int. Cl.
| | | |
|---|---|---|
| *A61F 2/80* | (2006.01) | |
| *A61F 2/78* | (2006.01) | |
| *A61F 2/50* | (2006.01) | |

(52) U.S. Cl.
CPC ............... *A61F 2/7812* (2013.01); *A61F 2/80* (2013.01); *A61F 2002/5053* (2013.01); *A61F 2002/802* (2013.01); *A61F 2002/805* (2013.01)

(58) Field of Classification Search
CPC ........... A61F 2/76; A61F 2/78; A61F 2/7812; A61F 2/80
See application file for complete search history.

(56) References Cited

U.S. PATENT DOCUMENTS

| | | |
|---|---|---|
| 980,457 A | 1/1911 | Toles |
| 1,398,824 A | 11/1921 | Abrams |

(Continued)

FOREIGN PATENT DOCUMENTS

| | | |
|---|---|---|
| AT | 369 978 B | 2/1983 |
| DE | 484 363 C | 10/1929 |

(Continued)

OTHER PUBLICATIONS

Extended European Search Report from EP Application No. 14161004.8, May 22, 2014, 6 pages.

(Continued)

*Primary Examiner* — Marcia Watkins
(74) *Attorney, Agent, or Firm* — Workman Nydegger

(57) ABSTRACT

A suspension liner sleeve adapted to provide an interface between a residual limb and a prosthetic socket, and having outer and inner surfaces. The liner sleeve includes an elongate, generally conical body portion formed from at least one material segment defining the liner outer surface. The at least one material segment being at least radially elastically extensible from a relaxed non-extended condition and including proximal and distal end areas. The liner sleeve includes a layer of polymeric material disposed on the at least one material segment and defining the liner sleeve inner surface, and a plurality of resilient seal elements protruding radially from the liner sleeve outer surface. The plurality of seal elements extend around at least one peripheral portion of the liner body portion. A pair of opposed annular recesses may be adjacently located above and below each of the at least one seal element.

8 Claims, 11 Drawing Sheets

Related U.S. Application Data continuation of application No. 11/654,549, filed on Jan. 18, 2007, now Pat. No. 8,034,120, which is a continuation-in-part of application No. 11/516,500, filed on Sep. 7, 2006, now Pat. No. 7,909,884, which is a continuation-in-part of application No. 11/135,354, filed on May 24, 2005, now Pat. No. 7,749,281, which is a division of application No. 10/690,545, filed on Oct. 23, 2003, now Pat. No. 7,025,793.

(60) Provisional application No. 60/434,669, filed on Dec. 20, 2002.

(56) References Cited

U.S. PATENT DOCUMENTS

| | | |
|---|---|---|
| 1,893,853 A | 1/1933 | Tullis |
| 2,325,656 A | 8/1943 | Brophy |
| 2,464,443 A | 3/1949 | Ganoe et al. |
| 2,530,285 A | 11/1950 | Catranis |
| 2,533,404 A | 12/1950 | Sharp et al. |
| 2,634,424 A | 4/1953 | O'Gorman |
| 2,671,225 A | 3/1954 | Schoene et al. |
| 2,689,351 A | 9/1954 | Schindler |
| 2,808,593 A | 10/1957 | Andersen |
| 3,393,407 A | 7/1968 | Kandel |
| 3,587,572 A | 6/1971 | Evans |
| 3,671,980 A | 6/1972 | Baird |
| 3,947,897 A | 4/1976 | Owens |
| 4,128,903 A | 12/1978 | Marsh et al. |
| 4,215,679 A | 8/1980 | Rustin |
| 4,311,317 A * | 1/1982 | Bartels .......... A61M 16/16 220/304 |
| 4,319,413 A | 3/1982 | Mattil |
| 4,347,204 A | 8/1982 | Takagi et al. |
| 4,474,573 A | 10/1984 | Detty |
| 4,635,626 A | 1/1987 | Lerman |
| 4,738,249 A | 4/1988 | Linman et al. |
| 4,767,735 A | 8/1988 | Ewen et al. |
| 4,885,828 A | 12/1989 | Kozlowski |
| 4,908,037 A | 3/1990 | Ross |
| 4,923,474 A | 5/1990 | Klasson et al. |
| 5,007,937 A | 4/1991 | Fishman et al. |
| 5,055,528 A | 10/1991 | Kioka et al. |
| 5,122,583 A | 6/1992 | Ewen et al. |
| 5,139,523 A | 8/1992 | Paton et al. |
| 5,163,965 A | 11/1992 | Rasmusson et al. |
| 5,169,161 A * | 12/1992 | Jones .......... F16J 15/025 277/615 |
| 5,226,918 A | 7/1993 | Silagy et al. |
| 5,244,716 A | 9/1993 | Thornton et al. |
| 5,314,496 A | 5/1994 | Harris et al. |
| 5,376,129 A | 12/1994 | Faulkner et al. |
| 5,376,131 A | 12/1994 | Lenze et al. |
| 5,387,245 A | 2/1995 | Fay et al. |
| 5,549,709 A | 8/1996 | Caspers |
| 5,571,208 A | 11/1996 | Caspers |
| 5,571,209 A | 11/1996 | Brown, Sr. |
| 5,593,454 A | 1/1997 | Helmy |
| 5,658,353 A | 8/1997 | Layton |
| 5,702,489 A | 12/1997 | Slemker |
| 5,718,925 A | 2/1998 | Kristinsson et al. |
| 5,728,168 A | 3/1998 | Laghi et al. |
| 5,728,170 A | 3/1998 | Becker et al. |
| 5,735,906 A | 4/1998 | Caspers |
| 5,830,237 A | 11/1998 | Kania |
| 5,885,674 A | 3/1999 | Maemoto et al. |
| 5,888,216 A | 3/1999 | Haberman |
| 5,888,230 A | 3/1999 | Helmy |
| 5,904,722 A | 5/1999 | Caspers |
| 5,931,872 A | 8/1999 | Lohmann |
| 5,972,036 A | 10/1999 | Kristinsson et al. |
| 5,980,577 A | 11/1999 | Radis et al. |
| 6,076,284 A | 6/2000 | Terlizzi |
| 6,136,039 A | 10/2000 | Kristinsson et al. |
| 6,149,691 A | 11/2000 | Fay et al. |
| 6,171,431 B1 | 1/2001 | Gallagher, Jr. et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,361,568 B1 | 3/2002 | Hoerner |
| 6,368,357 B1 | 4/2002 | Schon et al. |
| 6,406,499 B1 | 6/2002 | Kania |
| 6,468,938 B1 | 10/2002 | Govoni et al. |
| 6,485,776 B2 | 11/2002 | Janusson et al. |
| 6,508,842 B1 | 1/2003 | Caspers |
| 6,544,292 B1 | 4/2003 | Laghi |
| 6,554,868 B1 | 4/2003 | Caspers |
| 6,585,774 B2 | 7/2003 | Dean, Jr. et al. |
| 6,626,952 B2 | 9/2003 | Janusson et al. |
| 6,645,253 B2 | 11/2003 | Caspers |
| 6,706,364 B2 | 3/2004 | Janusson et al. |
| 6,726,726 B2 | 4/2004 | Caspers |
| 6,761,742 B2 | 7/2004 | Caspers |
| 6,852,269 B2 | 2/2005 | Eberle et al. |
| 6,926,742 B2 | 8/2005 | Caspers et al. |
| 6,929,125 B1 * | 8/2005 | Seamans .......... B65D 81/07 190/28 |
| 6,964,688 B1 | 11/2005 | Kania |
| 7,001,563 B2 | 2/2006 | Janusson et al. |
| 7,025,793 B2 | 4/2006 | Egilsson |
| 7,118,602 B2 | 10/2006 | Bjarnason |
| 7,144,429 B2 | 12/2006 | Carstens |
| 7,169,188 B2 | 1/2007 | Carstens |
| 7,169,189 B2 | 1/2007 | Bjarnason et al. |
| 7,235,108 B2 | 6/2007 | Carstens |
| 7,291,182 B1 | 11/2007 | Kania |
| 7,351,264 B2 | 4/2008 | Wilson |
| 7,427,297 B2 | 9/2008 | Patterson et al. |
| 7,592,286 B2 | 9/2009 | Morini et al. |
| 7,749,281 B2 | 7/2010 | Egilsson |
| 7,771,487 B2 | 8/2010 | Mantelmacher |
| 7,909,884 B2 * | 3/2011 | Egilsson .......... A61F 2/7812 623/33 |
| 8,034,120 B2 | 10/2011 | Egilsson et al. |
| 8,052,760 B2 * | 11/2011 | Egilsson .......... A61F 2/7812 623/33 |
| 8,097,043 B2 | 1/2012 | Egilsson |
| 8,372,159 B2 | 2/2013 | Mackenzie |
| 2001/0005798 A1 | 6/2001 | Caspers |
| 2001/0016781 A1 | 8/2001 | Caspers |
| 2002/0040248 A1 | 4/2002 | Karason |
| 2002/0087215 A1 | 7/2002 | Caspers |
| 2002/0091449 A1 | 7/2002 | Caspers et al. |
| 2002/0099450 A1 | 7/2002 | Dean, Jr. et al. |
| 2002/0165619 A1 | 11/2002 | Hellberg |
| 2002/0183859 A1 | 12/2002 | Houser |
| 2003/0181989 A1 | 9/2003 | Eberle et al. |
| 2003/0191539 A1 | 10/2003 | Caspers |
| 2004/0024322 A1 | 2/2004 | Caspers |
| 2004/0030411 A1 | 2/2004 | Caspers |
| 2004/0040248 A1 | 3/2004 | Vilnes |
| 2004/0098136 A1 | 5/2004 | Caspers |
| 2004/0122528 A1 | 6/2004 | Egilsson |
| 2004/0143345 A1 | 7/2004 | Caspers |
| 2004/0167638 A1 | 8/2004 | Caspers |
| 2004/0181290 A1 | 9/2004 | Caspers |
| 2004/0236434 A1 | 11/2004 | Carstens |
| 2004/0243251 A1 | 12/2004 | Carstens |
| 2004/0243252 A1 | 12/2004 | Carstens |
| 2005/0101693 A1 | 5/2005 | Arbogast et al. |
| 2005/0216095 A1 | 9/2005 | Egilsson |
| 2005/0240282 A1 | 10/2005 | Rush et al. |
| 2005/0240283 A1 | 10/2005 | Kania |
| 2005/0267598 A1 | 12/2005 | Bjarnason et al. |
| 2005/0267599 A1 | 12/2005 | Bjarnason |
| 2006/0212128 A1 | 9/2006 | Nachbar |
| 2007/0005149 A1 | 1/2007 | Egilsson et al. |
| 2007/0021295 A1 | 1/2007 | Morini et al. |
| 2007/0027556 A1 | 2/2007 | Wilson |
| 2007/0043450 A1 | 2/2007 | Pickering et al. |
| 2007/0061017 A1 | 3/2007 | Wilson |
| 2007/0123998 A1 | 5/2007 | Egilsson et al. |

(56) References Cited

U.S. PATENT DOCUMENTS

| | | |
|---|---|---|
| 2007/0179606 A1 | 8/2007 | Huyghe et al. |
| 2008/0147202 A1 | 6/2008 | Danzig et al. |
| 2008/0188949 A1 | 8/2008 | MacKenzie |
| 2008/0221705 A1 | 9/2008 | Scussel |
| 2008/0221706 A1 | 9/2008 | Scussel et al. |
| 2008/0269914 A1 | 10/2008 | Coppens et al. |
| 2009/0036999 A1 | 2/2009 | Egilsson et al. |
| 2009/0069171 A1 | 3/2009 | Sagae |
| 2009/0157196 A1 | 6/2009 | Danzig et al. |
| 2009/0198346 A1 | 8/2009 | Perkins et al. |
| 2009/0240344 A1 | 9/2009 | Colvin et al. |
| 2009/0306791 A1 | 12/2009 | Slemker et al. |
| 2010/0070051 A1 | 3/2010 | Carstens |
| 2010/0185300 A1 | 7/2010 | Mackenzie |
| 2010/0249950 A1 | 9/2010 | Bielefeld |
| 2010/0274364 A1 | 10/2010 | Pacanowsky et al. |
| 2010/0318196 A1 | 12/2010 | Egilsson |
| 2011/0029096 A1 | 2/2011 | Laghi |
| 2011/0035027 A1 | 2/2011 | McCarthy |
| 2011/0054635 A1 | 3/2011 | Watts |
| 2011/0071649 A1 | 3/2011 | McKinney |
| 2011/0077748 A1 | 3/2011 | Egilsson et al. |
| 2011/0118854 A1 | 5/2011 | Halldorsson |
| 2012/0041568 A1 | 2/2012 | Mackenzie |
| 2013/0053982 A1 | 2/2013 | Halldorsson |
| 2013/0138224 A1 | 5/2013 | Mackenzie |
| 2013/0197670 A1 | 8/2013 | Mackenzie |

FOREIGN PATENT DOCUMENTS

| | | |
|---|---|---|
| DE | 745 981 C | 5/1944 |
| DE | 813 190 C | 9/1951 |
| DE | 1 795 809 U | 9/1959 |
| DE | 2 060 239 A1 | 6/1972 |
| DE | 2 127 269 A1 | 12/1972 |
| DE | 2 540 138 A1 | 3/1977 |
| DE | 2 544 446 A1 | 4/1977 |
| DE | 3 221 920 A1 | 4/1983 |
| DE | 3 508 919 A1 | 9/1986 |
| DE | 9 419 208 U1 | 1/1995 |
| EP | 0 631 765 A1 | 1/1995 |
| EP | 1 572 043 A2 | 9/2005 |
| FR | 2 420 335 A1 | 10/1979 |
| FR | 2 539 616 A1 | 7/1984 |
| FR | 2 828 093 A1 | 2/2003 |
| GB | 263 377 A | 12/1926 |
| GB | 267 988 A | 3/1927 |
| GB | 826 041 A | 12/1959 |
| GB | 2 069 847 A | 9/1981 |
| GB | 2 087 727 A | 6/1982 |
| JP | H7-155343 A | 6/1995 |
| JP | H9-104714 A | 4/1997 |
| JP | 2637076 B2 | 8/1997 |
| JP | 2740503 B2 | 4/1998 |
| JP | H10-182740 A | 7/1998 |
| JP | 2001-055413 A | 2/2001 |
| JP | 2002-500697 A | 1/2002 |
| JP | 2006-176565 A | 7/2006 |
| JP | 2006-316160 A | 11/2006 |
| JP | 2006-528271 A | 12/2006 |
| JP | 3984304 B2 | 10/2007 |
| WO | 97/34548 A2 | 9/1997 |
| WO | 00/74611 A2 | 12/2000 |
| WO | 01/54631 A1 | 8/2001 |
| WO | 01/67842 A1 | 9/2001 |
| WO | 02/26158 A2 | 4/2002 |
| WO | 03/024367 A2 | 3/2003 |
| WO | 03/024370 A1 | 3/2003 |
| WO | 03/039398 A2 | 5/2003 |
| WO | 03/099173 A1 | 12/2003 |
| WO | 2004/060136 A2 | 7/2004 |
| WO | 2010/085336 A1 | 7/2010 |
| WO | 2013/005735 A1 | 1/2013 |

OTHER PUBLICATIONS

"Silicone-Only Suspension (SOS) with Socket-Loc and the Ring for the Lower Limb", found at, http://www.oandp.org/jpo/library/1995_01_002.asp. Journal of Prosthetics and Orthotics 1995;vol. 7, Num 1, p. 2.

Iceross Comfort Locking/Cushion Product Information Brochure, Mar. 27, 2009, 3 Pages.

Iceross Dermo, Product Information Sheets from Internet, http://www.ossur.com/prosthetics/liners/dermo, Mar. 27, 2009, 2 Sheets.

Military inStep: Prosthetic Socks and Liners, Product Information Sheets from Internet, http://www.amputee-coalition.org/military-instep/prosthetic-socks, Mar. 27, 2009, 3 Pages.

Prosthetic & Orthotic Update NewsLetter, No. 32, Internet Search Conducted Mar. 27, 2009, 4 Pages.

Walopur Platilon U, Product Information Brochure of Epurex Films GmbH & Co., KG, Internet Search Result Conducted Mar. 27, 2009, 2 Pages.

International Search Report and Written Opinion Issued in PCT/US2012/051645, Dec. 3, 2012.

Supplementary EP Search Report from EP Application No. 07837275.2, Feb. 19, 2014, 6 pages.

* cited by examiner

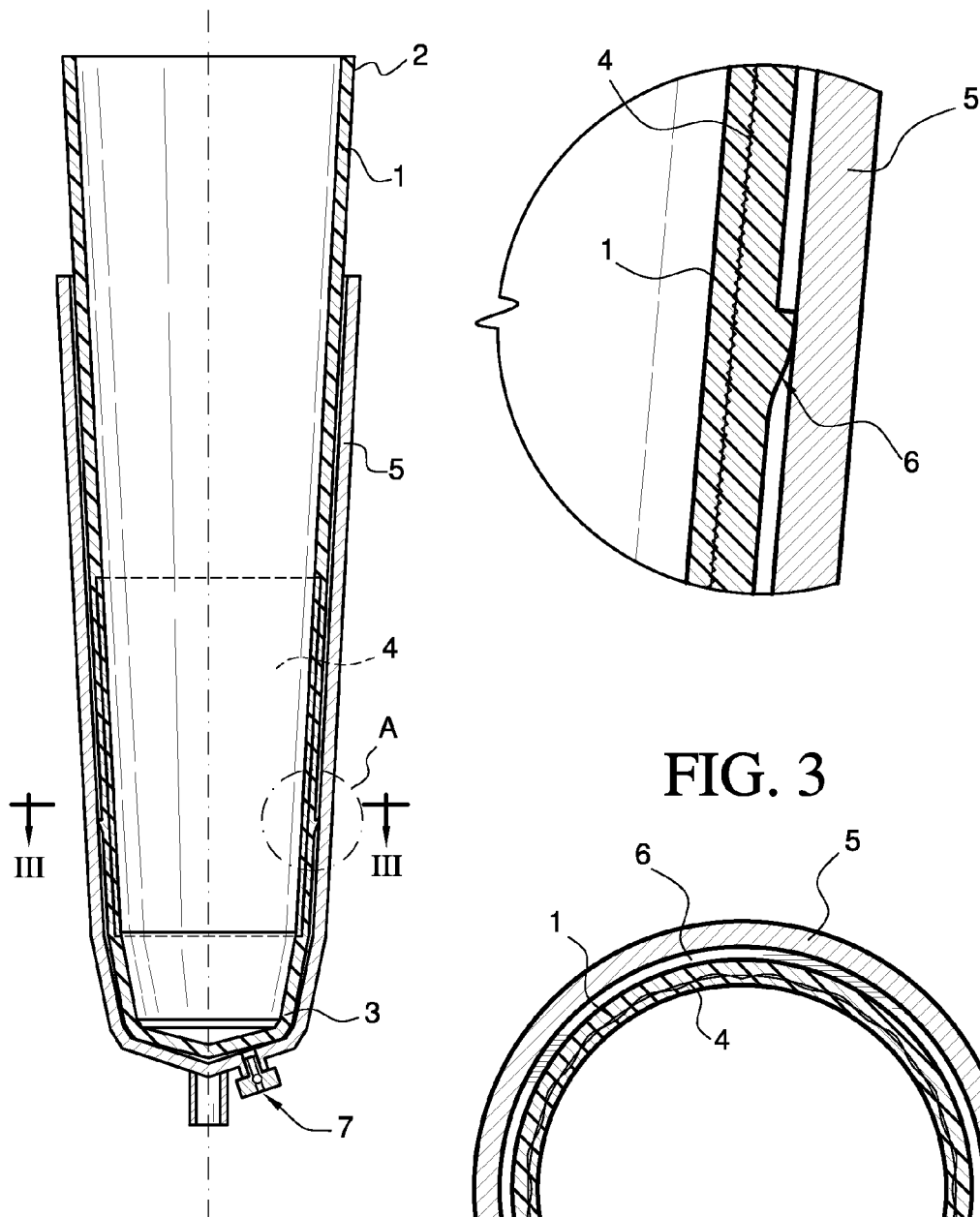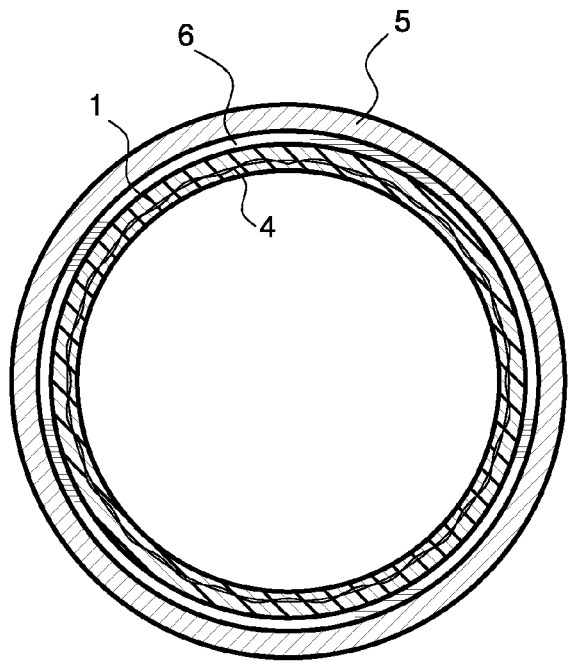

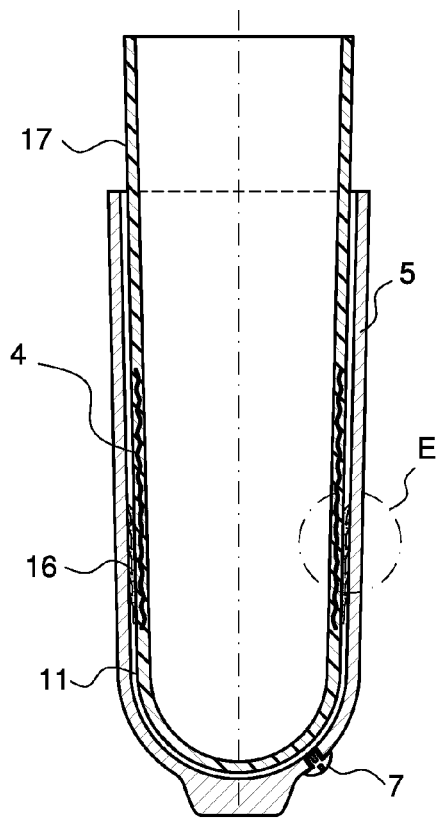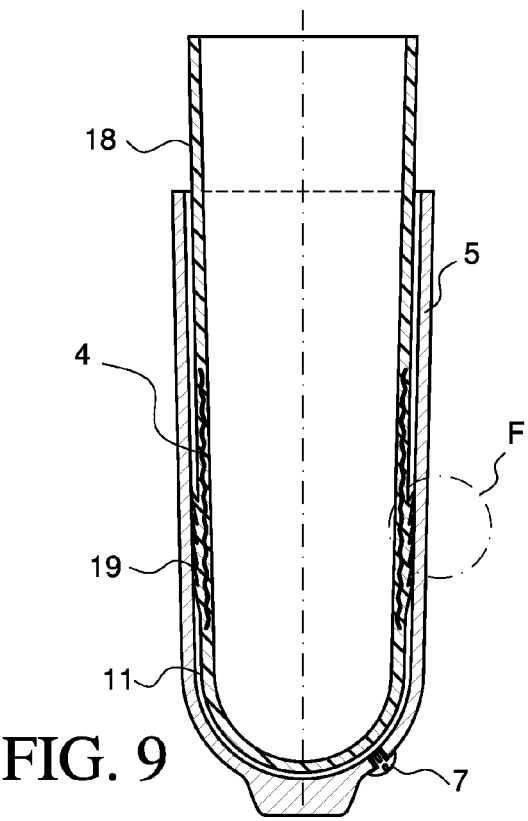
FIG. 8
FIG. 9
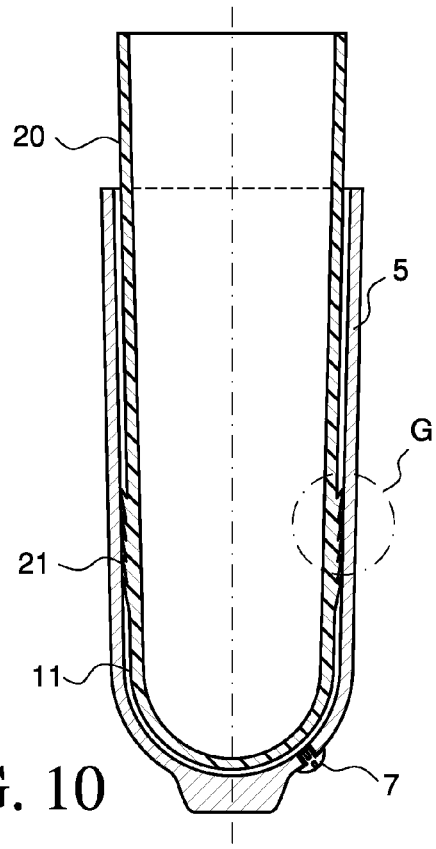
FIG. 10

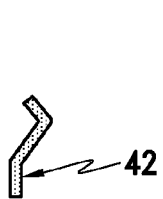 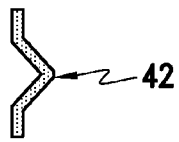 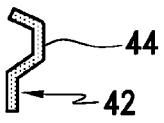 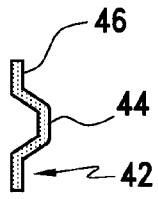
FIG. 21   FIG. 22   FIG. 23   FIG. 24
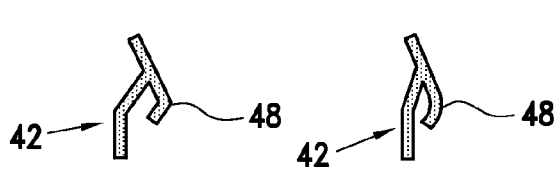 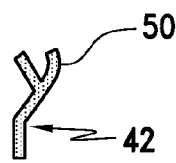 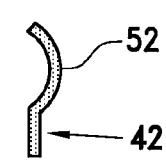
FIG. 25   FIG. 26   FIG. 27   FIG. 28
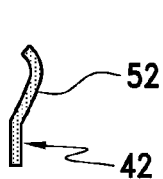 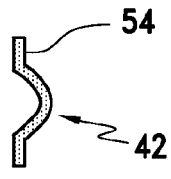 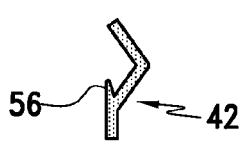 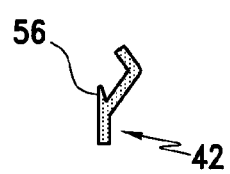
FIG. 29   FIG. 30   FIG. 31   FIG. 32
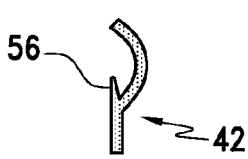 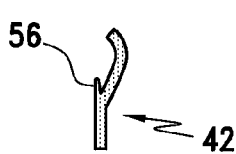 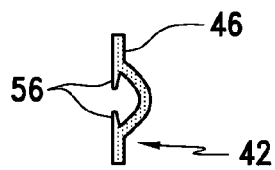
FIG. 33   FIG. 34   FIG. 35

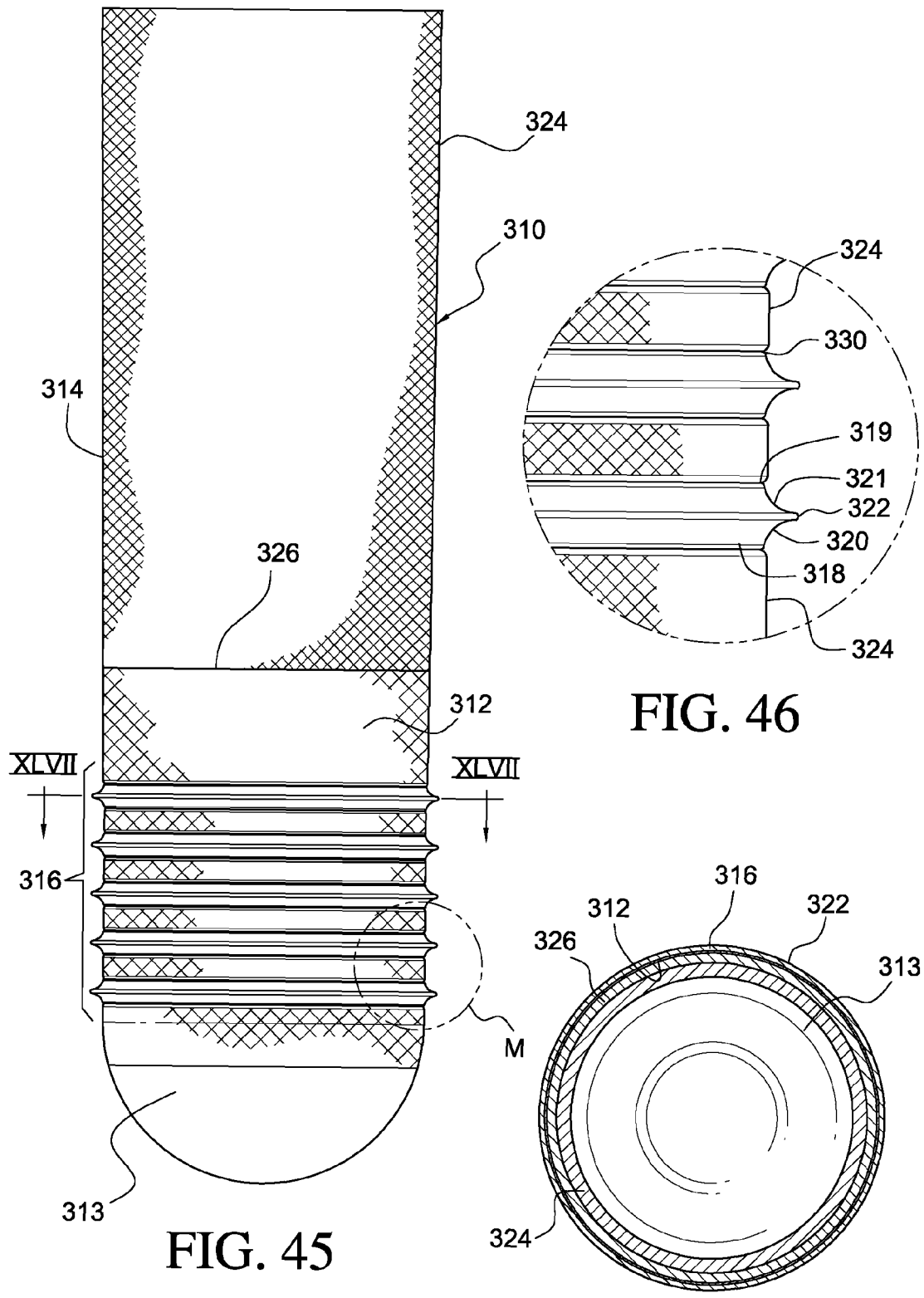

SUSPENSION LINER SYSTEM WITH SEAL

BACKGROUND a. Field of the Invention

This invention relates to suspension liner sleeves adapted to provide an interface between a residual limb and a prosthetic socket.

b. Discussion of Related Art

The use of suspension liner sleeves adapted to provide a soft, flexible interface between a residual limb of an amputee and a hard socket to which a prosthetic device is secured is known in the art generally, as exemplified by U.S. Pat. No. 4,923,474 granted May 8, 1990 to Klasson and Kristinsson. Such liner sleeves are typically made of an air impermeable elastomer material such as silicone and may include a reinforcement layer intermediate the inner and outer surfaces of the liner sleeve body portion or externally thereof to provide resistance against axial elongation of the elastomer constituting the liner sleeve body. Such reinforcement typically does not restrict radial distension or stretching of the liner sleeve body.

In accordance with prior art teachings, such liner sleeves, sometimes called suspension sleeves, may function to secure the residual limb within the prosthetic socket member once the residual limb and sleeve are inserted into the socket in close-fitting relationship by isolating the distal end area of the hard socket from the atmosphere. Upon application of a pulling force on the liner sleeve relative to the socket, a suction is created in the distal end of the socket tending to retain the liner sleeve within the socket. Appropriate devices are usually provided to enable expulsion of air between the distal end of the liner sleeve and the hard socket, and to isolate the distal end of the hard socket member from the atmosphere after the liner sleeve with a residual limb has been fully inserted within the socket member.

In some applications, the liner sleeve is provided with an umbrella at its distal end and a threaded socket for receiving a prosthetic securing pin member which then extends through an axial opening in the distal end of the hard socket member for securing the socket member relative to a prosthetic device mounted to the distal end of the socket member.

In other applications, the prosthetic device is secured to the exterior of the distal end of the hard socket member and the sleeve member is fully contained within the hard socket member.

The elastomer constituting the liner sleeve member frictionally engages and remains attached to the skin of a residual limb so that the limb is retained within the hard socket member in a comfortable, non-irritating manner. The liner sleeve may be thickened to provide cushioning effect between the residual limb and the hard socket, which is typically custom made to closely fit the residual limb. Liner sleeves of this kind are used for both trans-tibial (TT) amputees as well as trans-femoral (TF) amputees. That is, the liner sleeves may be utilized for applications above the knee or below the knee of the amputee.

In other applications, it may be desired to more positively secure the liner sleeve within the socket by creating a hypobaric (vacuum) pressure within the distal end of the hard socket between such distal end and the distal end of a liner sleeve inserted into the socket with a residual limb contained within the liner sleeve. The hypobaric pressure may be maintained at the distal end of the hard socket and the interior of the socket at its distal end will be isolated from atmosphere during normal retention of the sleeve liner within the socket. Opening the distal end of the socket to atmosphere releases the vacuum or hypobaric pressure within the socket to enable simple withdrawal of a residual limb with a liner sleeve thereon from the socket.

A pump or other device may be utilized to evacuate the distal end of the socket between the distal end of a liner sleeve and the distal end of a socket. A valve or other appropriate device typically is used to open and close the distal end of a socket to surrounding atmosphere.

Various arrangements are known in the prior art for providing an appropriate seal between the exterior of the liner sleeve and the interior of the hard socket including external air impermeable sleeves covering the interface area between the proximal end of the hard socket and the adjacent liner sleeve body.

In trans-femoral applications, the sealing between a liner sleeve and a socket is generally simpler and easier to execute than sealing a trans-tibial liner sleeve against the inner surface of a socket because in the latter situation, the residual limb contains more bony protuberances and irregular shapes that are difficult to effectively seal, particularly if it is desired to simply use the material of the elastomeric liner sleeve as the sealing element.

SUMMARY

In accordance with the present invention, an elastomeric liner sleeve having an elongate, generally conical, air impermeable body portion that is typically freely radially elastically distensible from a relaxed non-extended condition and including proximal and distal end areas is provided with a resilient seal element protruding radially from a liner sleeve body portion between its proximal and distal end areas, such resilient seal element extending around an entire peripheral portion of the liner sleeve body portion.

In one embodiment, a suspension liner system adapted to provide an interface between a residual limb and a prosthetic socket, the liner sleeve including an elongate generally conical liner sleeve including proximal and distal end areas, and a sealing member arranged to removably fit onto the distal end area of the liner sleeve. The sealing member has proximal and distal end areas, and defines a resilient seal element located at the proximal end area and a receiving portion formed from the distal end area. The seal element outwardly protrudes relative to the receiving portion of the liner sleeve and is arranged for deflection against the liner sleeve.

According to variations of the embodiment, the liner sleeve may have a recessed portion extending around at least a peripheral portion of the liner sleeve to accommodate the seal element of the sealing member. Also, in another variation, the liner sleeve may be provided with reinforcement material that corresponds to the distal end area of the liner sleeve.

In other embodiments, the liner sleeve may include a plurality of resilient seal elements that protrude radially from the liner body portion of the liner sleeve. These seal elements may be formed integrally with the silicone inner layer of the liner sleeve, or may be secured to elastic matrix material of the liner sleeve.

In variations, the liner sleeve may include two different segments of matrix material, reinforcing material or covering material, wherein a first material segment has greater stiffness than the second material segment. The plurality of seals may be disposed along the first material segment. The first and second material segments may be divided by a common seam that varies in distance relative to the distal and proximal end areas of the liner sleeve to provide varying degrees of stiffness.

In use, a residual limb is placed within the liner sleeve body portion according to the invention and both the residual limb and the liner sleeve body portion are inserted within a hard socket of a prosthetic system so that the peripheral seal element engages an inner wall of the hard socket to isolate the distal end area of the hard socket from surrounding atmosphere. Creation of a hypobaric pressure within the distal end area of the hard socket or simple evacuation or venting of air between the distal end area of the liner sleeve body portion and the distal end of the hard socket followed by sealing off the area between the liner sleeve body portion and the internal distal end of the socket serves to effectively retain the liner sleeve within the socket of the prosthetic system, with the seal effectively isolating the distal end of the hard socket externally of the liner sleeve from atmosphere.

Whether a hypobaric pressure is created within the distal end area of the hard socket or if the distal end is merely isolated from atmosphere, withdrawal of the liner sleeve body portion and the residual limb contained therein will be resisted strongly by the creation of or maintenance of a suction between the distal end of the liner sleeve body portion and the interior distal end area of the hard socket when a pulling force tending to extricate the liner sleeve body portion from the prosthetic socket is applied.

The suction may be released between the hard socket and the liner sleeve simply by exposing the interior distal end area of the hard socket to atmosphere.

The seal element serves to provide a positive sealing effect by its resilient compression between the inner wall of the hard socket and the liner sleeve body portion due to the radial force of the residual limb within the liner sleeve body portion. The peripherally extending seal takes up irregularities between the exterior of the liner sleeve and the interior of the socket irrespective of bony protuberances, irregularities and non-cylindrical forms of the residual limb. Because the socket is already configured to closely approximate the exterior shape of the residual limb, the seal simply follows the contour of the inner surface of the socket to isolate the distal end of the socket from atmosphere when the liner sleeve is inserted into the socket.

In accordance with one embodiment, the liner sleeve includes an elongate, generally conical body portion formed from at least one material segment that is at least radially elastically extensible from a relaxed non-extended condition. The liner sleeve includes a plurality of resilient seal elements that protrude radially from the liner body portion such that the plurality of seal elements extend around at least one outer peripheral portion of the liner body portion.

In a variation of the embodiment, the seal elements are formed from a polymeric material secured to the at least one material segment. The at least one material segment may include a first material segment generally provided at the distal end area of the liner, and a second material segment secured to the first material segment. The first material segment preferably has stiffness greater than the stiffness of the second material segment. The second material segment may be secured to the first material segment along a seam varying in distance relative to the distal and proximal end areas.

In a variation of the seal elements, the seal elements may each define at least one curvilinear section extending from the liner body portion to a peak defined as the outermost extending portion of the seal element. Alternatively, the seal elements each define a peak defined as the outermost extending portion of the seal element, a distal curvilinear section extending from the peak to the liner body portion, and a proximal curvilinear section extending from the peak to the liner body portion. A pair of opposed annular recesses may be adjacently located above and below each of the at least one seal element.

In another embodiment of the liner sleeve, the liner body portion includes first and second layers of polymeric material disposed along the at least one material segment. The first layer of polymeric material is secured directly to the at least one material segment and has a greater hardness than the second layer of polymeric material. The plurality of seal elements may be formed from the second layer of polymeric material as it locally extends through the at least one material segment.

BRIEF DESCRIPTION OF THE DRAWINGS

These and other features, aspects, and advantages of the present invention will become better understood with regard to the following description, appended claims, and accompanying drawings where:

FIG. 1 is a vertical sectional view of a prosthesis system including a hard socket, an elastomer liner sleeve having a reinforcement material embedded in the liner sleeve body portion and further including a peripheral seal element integrated with the elastomer liner sleeve.

FIG. 2 is a sectional view corresponding to detail A in FIG. 1.

FIG. 3 is a cross-sectional view taken along line III-III in FIG. 1.

FIGS. 4-10 are vertical sectional views of a prosthesis system corresponding to FIG. 1 wherein alternate forms of peripheral seal elements are illustrated.

FIGS. 21-35 are vertical sectional views of alternate forms of the peripheral seal element illustrated in FIG. 17.

FIG. 45 is an elevational view of another embodiment of a prosthetic liner.

FIG. 46 is a sectional view corresponding to detail M in FIG. 45.

FIG. 47 is a sectional view taken along line XLVII in FIG. 45.

DETAILED DESCRIPTION OF VARIOUS EMBODIMENTS

Figure 4:
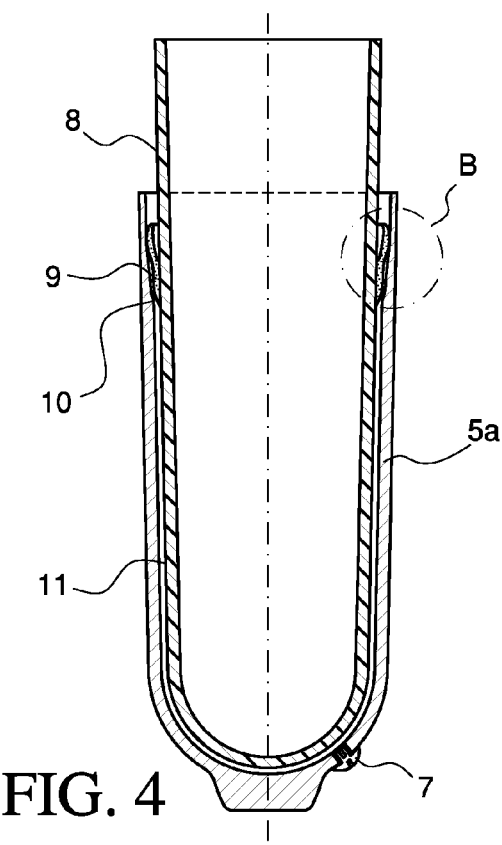

With reference to FIG. 1, an elastomer liner sleeve body portion 1, for example made of silicone, is formed as an elongate, generally conical member as is well known in the art and as is further described in U.S. Pat. No. 4,923,474, the entirety of which is incorporated herein by reference.

The liner sleeve body portion may be formed of various elastomer materials that are known to those skilled in the art and that are typically used for the manufacture of prosthetic liner sleeves.

The liner sleeve extends between a proximal end 2 and a distal end area 3. The liner sleeve body portion is soft and at least radially distensible elastically. The liner sleeve also may be elastically distensible axially or may have limited axial elasticity or at least a greater elastic stiffness (resistance to distension) in an axial sense as compared with its radial elasticity, but such anisotropy is optional.

If it is desired to increase the axial stiffness of the liner sleeve body portion 1, a reinforcement material 4 is integrated into the elastomer of the liner sleeve body portion, for example in the manner described in U.S. Pat. No. 4,923,474. Various reinforcement materials may be utilized to limit axial distension of the liner sleeve body portion and typically a material that is axially stiff but radially compliant is preferred. Thus, the combination of the elastomer material constituting the liner sleeve body portion and the reinforcement body material results in a liner sleeve that resists elongation in the axial direction in the event that tension is applied to the liner sleeve material while the sleeve is fully radially compliant elastically so as not to unduly compress a residual limb contained within the liner sleeve or restrict its ability to fill the hard socket member. The reinforcement material 4 alternatively may be located externally of the elastomer, such as a textile cover on the elastomer liner sleeve body, for example.

The liner sleeve 1 is typically donned on a residual limb and the limb and sleeve are then inserted into the prosthetic socket 5 which is typically rigid or hard in order to carry loads transferred from a prosthetic device attached to the socket to the residual limb and vice-versa.

The softer elastomer of the liner sleeve body portion adheres to the skin of a residual limb frictionally to thereby secure the limb within the sleeve. The liner sleeve, on the other hand, remains contained within the hard socket 5 after it has been fully inserted to the distal end area of the hard socket by effectively isolating the interior of the hard socket 5 from atmosphere.

Any pulling forces applied to the liner sleeve will result in a suction being created between the distal end of the liner sleeve and the interior of the hard socket at its distal end area. The increased stiffness in an axial sense created by the reinforcement material minimizes pumping action on the residual limb and creates a stiffer interface between the residual limb and the liner sleeve in the area occupied by the reinforcement material.

In accordance with the embodiment illustrated in FIG. 1, the reinforcement material 4 extends over a limited distal end area of the liner sleeve, but could extend fully around the distal end area of the liner sleeve, if desired, as shown, for example, in U.S. Pat. No. 4,923,474, and up to the proximal end 2 of the liner sleeve.

To further enhance isolation of the distal end area of the hard socket from atmosphere, a seal element 6 associated with the liner sleeve is provided. The seal element 6 could be formed of the same silicone material as the liner sleeve body portion 1 and created integrally in one piece with the liner sleeve body portion 1 during molding or forming of the liner sleeve body portion 1, or, alternatively, could be formed separately of a softer or stiffer material or a material more suitable for a seal than the material forming the liner sleeve body portion, and then secured to the liner sleeve.

The seal element 6 may be tapered outwardly from its distal end towards its proximal end to facilitate insertion of the liner sleeve body portion 1 into the hard socket 5 and tends to resist outward movement of the liner sleeve from the hard socket. Also, the form of seal element 6 preferably provides an increased sealing force between the liner sleeve 1 and the hard socket 5 when the liner sleeve 1 is moved in a direction tending to withdraw it from the hard socket, or in other words, the seal element 6 seals more effectively in a direction towards the liner sleeve distal end when subjected to a pressure differential where a lower pressure exists towards the distal side of the seal as compared to the proximal side thereof.

If desired, the seal element 6 could be formed as a separate element or assembly of elements attached to or otherwise secured to the liner sleeve body portion 1, as will be described below. It will be apparent that any manufacturing technique known to those skilled in the art could be utilized to create an enlarged seal element 6 surrounding the peripheral area of the liner sleeve body portion 1 at an area thereof between the proximal and distal end areas 2, 3 of the liner sleeve body portion 1 so that, upon insertion of the liner sleeve body portion into a hard socket 5, the seal 6 isolates the distal end area of the interior of the hard socket 5 from atmosphere between the seal 6 and the distal end area of the hard socket 5. While a single seal element may be utilized in accordance with the present invention, a plurality of seal rings 6 secured to the liner sleeve could be utilized to provide enhanced sealing effect, as will be described below.

When the liner sleeve body portion 1 is fully inserted into the socket 5, the seal 6 fully isolates the interior of the socket distal end area from atmosphere until communication is provided between the interior of the socket distal end and atmosphere.

To permit purging of air from the distal end of the socket 5 while the liner sleeve body portion 1 and its associated seal 6 are inserted into the socket, an appropriate one way valve element 7 may be provided, or a valve capable of opening and closing manually may be used to isolate the interior of the distal end of the socket 5 from atmosphere.

It will be apparent that, when the liner sleeve body portion 1 is fully inserted into the socket 5 with the seal 6 isolating the distal end area of the socket 5 from atmosphere, all pulling loads tending to withdraw the liner sleeve from the socket will result in a suction being created between the distal end area of the liner sleeve 1 and the distal end of the socket 5. The seal 6 further enhances and maintains the suction between the liner sleeve body portion 1 and the socket 5. The presence of the reinforcement material in the vicinity of the seal 6 further enhances the function of the seal element 6 in maintaining the distal end area of the socket 5 isolated from atmosphere when the residual limb and its associated liner sleeve body portion 1 have been fully inserted into the socket due to better distribution of loads between the socket 5, the liner sleeve body portion, and a residual limb.

If desired, a hypobaric pressure could be created between the distal end area of the liner sleeve body portion 1 and the distal end of the socket 5 by attaching a pump or other device that enables evacuation of atmosphere between the seal 6 and the distal end of the socket 5.

With reference to FIGS. 4-16, various alternative preferred forms of liner sleeve body portions, seal elements and hard socket interior configurations are illustrated by way of example.

Figure 11:
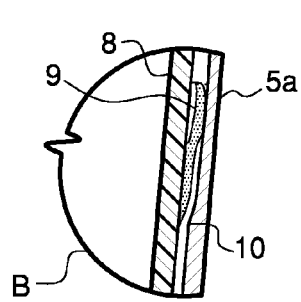
FIGS. 11-16 are sectional views corresponding respectively with sections B, C, D, E, F, and G of FIGS. 4, 6, 7, 8, 9 and 10.
Figure 12:
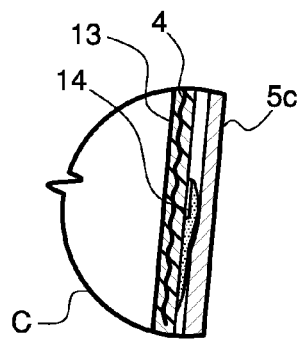

In FIG. 4, liner sleeve body portion 8 comprising an air-impermeable elastomeric material such as silicone is provided with a peripheral seal element 9 shown in more detail in FIG. 11. The seal element 9 is formed as a separate element from the liner sleeve body portion 8 and is securely attached thereto by appropriate bonding techniques that may include adhesive, heat seal, etc. In this instance, the hard socket 5a is provided with a slightly stepped portion 10 that enhances cooperation between the interior of the hard socket 5a and the seal element 9. The stepped portion 10 is not required but is optional. In this example, the seal element 9 includes a cantilevered end portion facing towards the proximal side of the liner sleeve body portion 8 to thereby enhance the ability of the seal element 9 to freely flex when a pressure differential exists on either side of the seal element 9. It will be apparent that when a higher pressure exists on the proximal side of the seal element 9 as compared with the distal side thereof, the seal element 9 will tend to expand outwardly against the interior surface of the hard socket 5a and a radial sealing force exerted by the seal will increase commensurately with the pressure differential. On the other hand, the properties of the seal and the interior wall of the hard socket 5a are such that the amputee may readily withdraw the liner sleeve body portion 8 from the hard socket 5a upon gentle pulling of the liner sleeve away from the hard socket, optionally while opening valve 7 to expose the isolated region 11 between the distal portion of the liner sleeve body portion 8 and the distal end area of the hard socket 5a to atmosphere.

Figure 5:
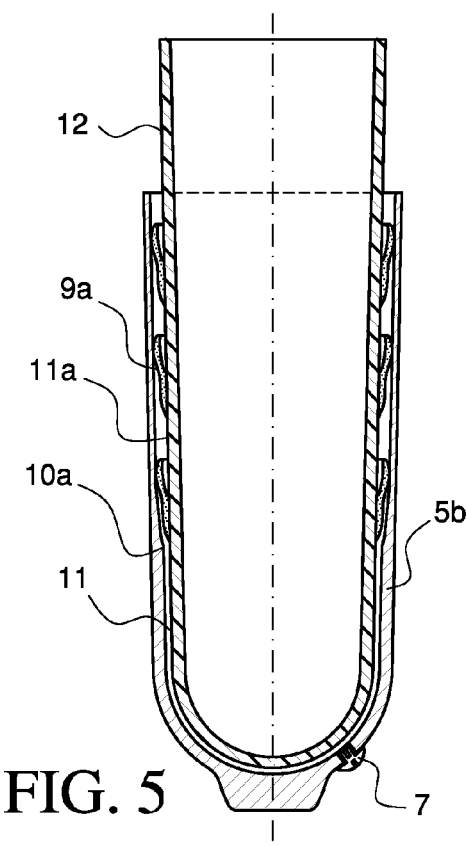

In FIG. 5, liner sleeve body portion 12 is provided with multiple, axially spaced seal elements 9a corresponding to seal element 9 in FIG. 4. This provides enhanced sealing between the liner sleeve body portion 12 and the interior of the hard socket 5b due to the multiple sealing surfaces provided and furthermore provides additional spaces 11a that are isolated from atmosphere to thereby enhance the suction effect between the liner sleeve body portion 12 and the hard socket 5b. The stepped portion 10a of the hard socket interior wall is located at a more distal region of the hard socket as compared with the stepped portion 10 in FIG. 4.

Figure 6:
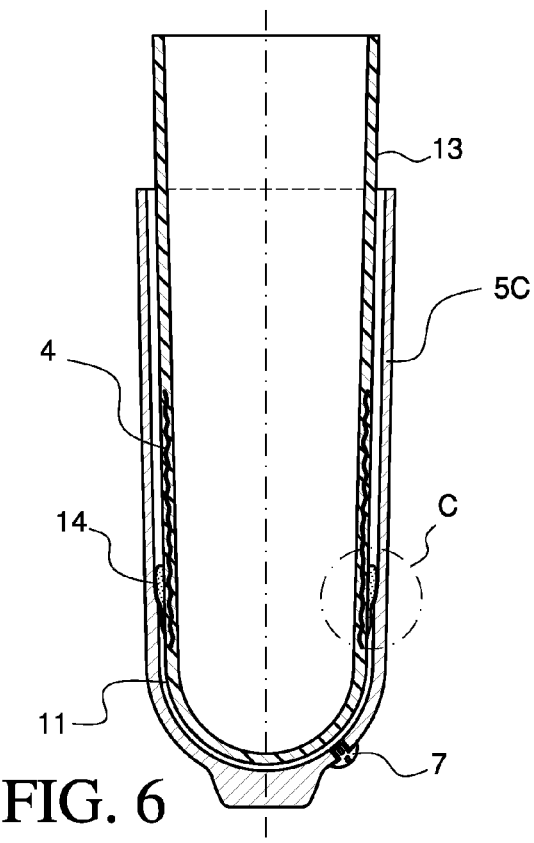

In FIG. 6, liner sleeve body portion 13 is provided with a single peripherally extending seal element 14 located towards the distal region of the liner sleeve body portion 13. The seal element 14 is formed separately from the liner sleeve body portion 13 and is secured thereto in the manner described above with respect to seal element 9 in FIG. 4. In accordance with this example, a reinforcement material 4 as described above in the example shown in FIG. 1 is provided to limit axial distension of the liner sleeve body portion 13, the reinforcement material being located in the vicinity of the seal element 14 and extending in a proximal direction relative thereto within the liner sleeve body portion 13. The seal element 14 and its relationship with the hard socket 5c in this example, the liner sleeve body portion 13 and the reinforcement material 4 are shown in more detail in FIG. 12.

Figure 7:
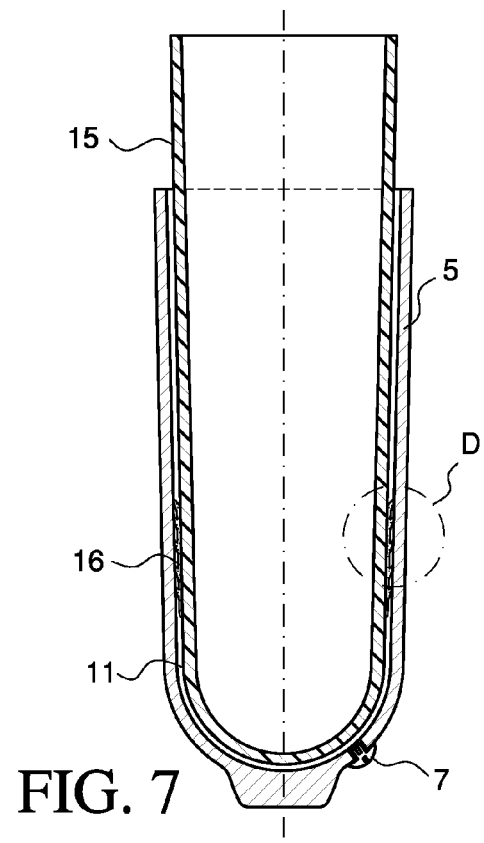
Figure 13:
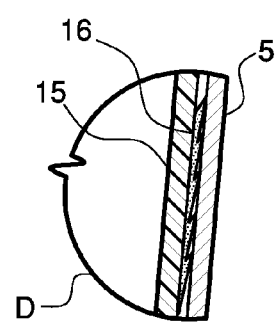
Figure 14:
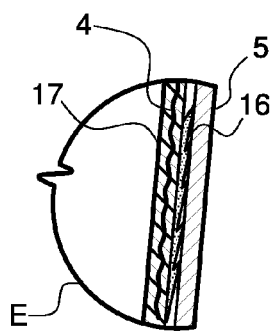

In FIG. 7, liner sleeve body portion 15 is provided with a seal assembly 16 which is shown in more detail in FIG. 13. In this example, the sleeve element 16 may be formed as a strip of material having radially bendable flaps constituting seal surfaces that, when exposed to differential pressure, will bend radially outwardly to engage the interior of the hard socket 5, which may correspond in shape to the hard socket 5 illustrated in FIG. 1. The seal element 16 may be secured to the liner sleeve body portion 15 by bonding, heat sealing, or any other appropriate bonding technique that will be readily apparent to a person skilled in the art.

In FIG. 8, liner sleeve body portion 17 is provided with a peripheral seal element 16 which is similar to the seal element described in FIG. 13, and a reinforcement material 4 is provided in the liner sleeve body portion 17 in a manner corresponding to that described previously with regard to FIG. 6.

Figure 15:
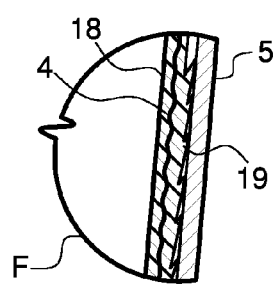
Figure 16:
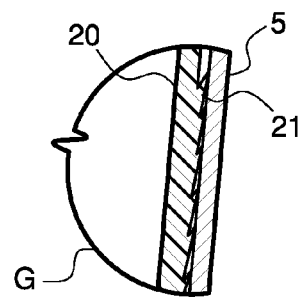

In FIG. 9, liner sleeve body portion 18 is provided with an integral peripherally extending seal element 19 that is shown in more detail in FIG. 15. The seal element 19 is integrally formed in one piece with the liner sleeve body portion 18 and comprises multiple sealing surfaces inclined radially outwardly and upwardly as shown in FIG. 15. Each radially outwardly extending element includes a sealing surface that engages the interior wall of the hard socket 5 in a manner similar to that described previously in connection with the seal elements 9, 9a, 15 and 16. That is, the form of the seal tends to increase sealing forces when the seal element is exposed to a pressure differential between the proximal and distal sides of the seal element, with the higher pressure existing towards the proximal end of the seal element. In this embodiment, a reinforcement material 4 is provided in the liner sleeve body portion 18 in the vicinity of the peripheral seal 19 and extending proximally relative thereto.

In FIG. 10, liner sleeve body portion 20 is provided with a peripheral seal 21 corresponding to seal 19 described above in connection with FIG. 9. A reinforcement material is not provided in this example. The interior of the hard socket 5 is not provided with a stepped portion in this example, although a stepped portion corresponding to the stepped portion 10 could be provided at the distal end area of the seal 21 when the liner sleeve body portion 20 is fully inserted in the hard socket 5 if desired.

With reference to FIGS. 17-20, an alternative preferred form of a liner sleeve and seal element is illustrated.

Figure 17:
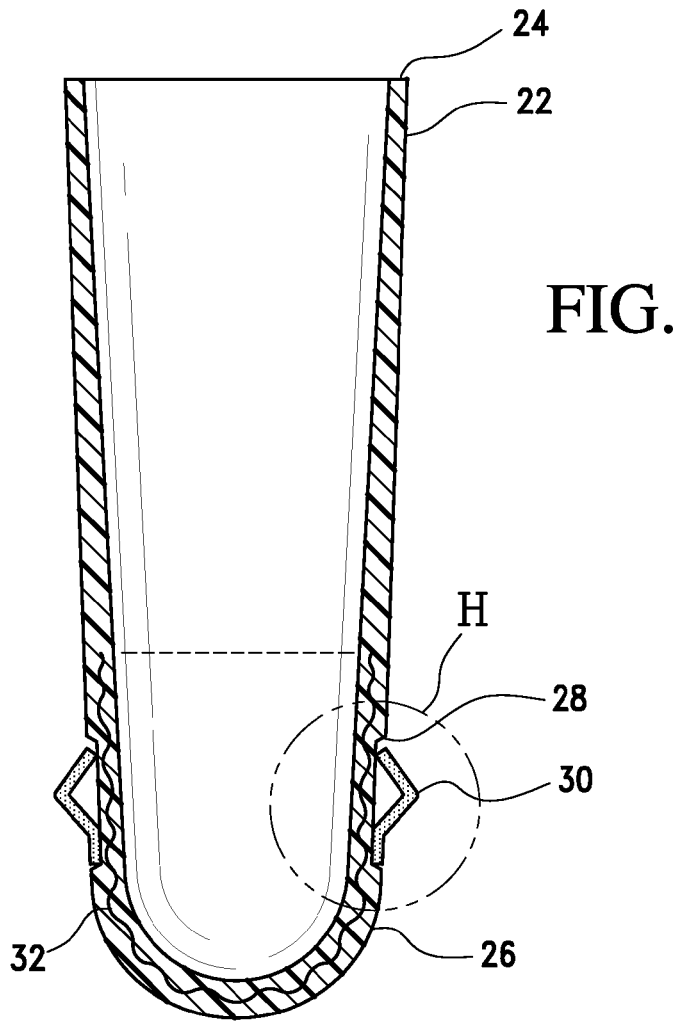
FIG. 17 is a vertical sectional view of an alternate form of an elastomer liner sleeve including a reinforcement material embedded in the liner sleeve body portion and a peripheral seal element secured to the elastomer liner sleeve in a recessed portion of the elastomer liner sleeve.

In FIG. 17, liner sleeve body portion 22 having a proximal end 24 and a distal end area 26 is provided with a recessed portion 28 and a peripheral seal element 30 radially protruding from the recessed portion 28. The recessed portion 28 extends continuously around a peripheral portion of the liner sleeve body portion 22 between the proximal and distal end areas 24, 26. The recessed portion 28 of the liner sleeve body portion 22 is configured with a length, width and depth to accommodate compression of the seal element 30. The liner sleeve body portion 22 may include a reinforcement material 32 that extends substantially around the distal area 26 of the liner sleeve body portion 22 and preferably extends at least to the seal element 30. The placement of the reinforcement material 32 is not limited to the distal end area of the liner sleeve body portion, and may extend upwardly to the proximal end 24 of the liner sleeve body portion 22.

Figure 18:
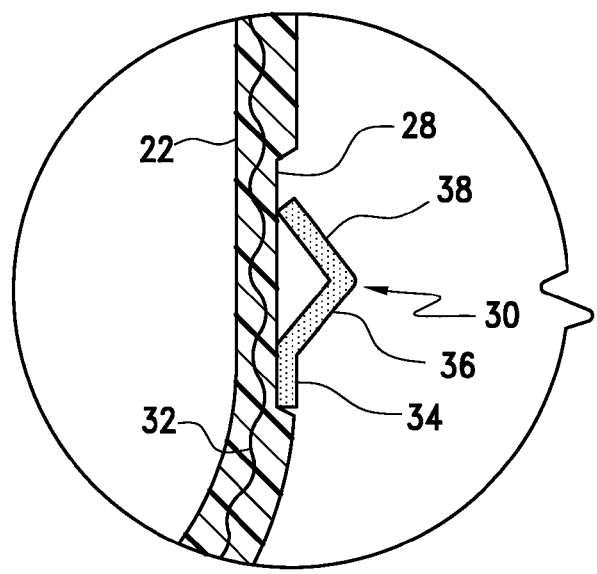
FIG. 18 is a sectional view corresponding to detail H in FIG. 17.

As illustrated in FIG. 18, the seal element 30 of this embodiment is formed as a separate element from the liner sleeve body portion 22, and is provided with a base member 34 that is positioned within the recessed portion 28 and is securely attached to the liner sleeve body portion 22 by appropriate bonding techniques that may include adhesive, heat seal, etc. The base member 34 is preferably parallel to the outer periphery of the liner sleeve body portion; however it will be understood that it is not limited to this orientation. The seal element 30 includes a radially outwardly pitched member 36 that extends from a proximal end of the base member 34 and is directed towards the proximal end 24 of the liner sleeve body portion 22 at an angle relative to the base member 34. The seal element 30 also includes a radially inwardly pitched member 38 that connects to a proximal end of the outwardly pitched member 36, and is directed towards the proximal end 24 of the liner sleeve body portion 22 at an angle relative to the base member 34.

Figure 19:
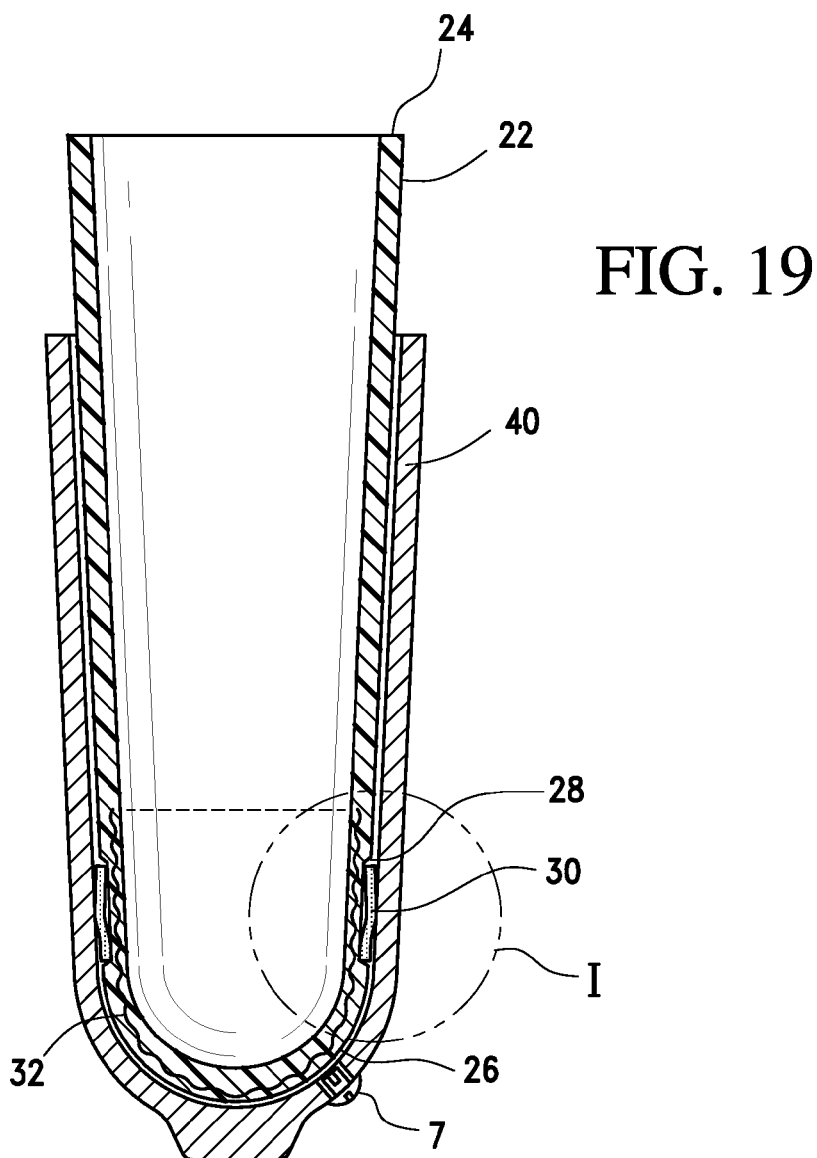
FIG. 19 is a vertical sectional view of an alternate prosthesis system including the liner sleeve of FIG. 17.

In FIG. 19, the liner sleeve body portion 22 is shown as being donned on a residual limb and the limb and liner sleeve body portion are inserted into a prosthetic hard socket 40. Preferably, the hard socket 40 includes a valve 7 located at a distal end area thereof that is of the type described above in the preceding embodiments of the present invention. When inserted in the hard socket 40, the seal element 30 is compressed so as to lie at least partially within the recessed portion 28 and bridges a seal between the liner sleeve body portion 22 and the hard socket 40. In a compressed state, the angles at which the outwardly and inwardly pitched members 36, 38 of the seal element 30 extend relative to the base member 34 are substantially less than when the liner sleeve body portion 22 is not inserted into the hard socket 40.

It will be understood that when compressed, at least a portion of the seal element should radially distend at least a distance from the recessed portion to sufficiently bridge the seal between the liner sleeve body portion and a hard socket.

Figure 20:
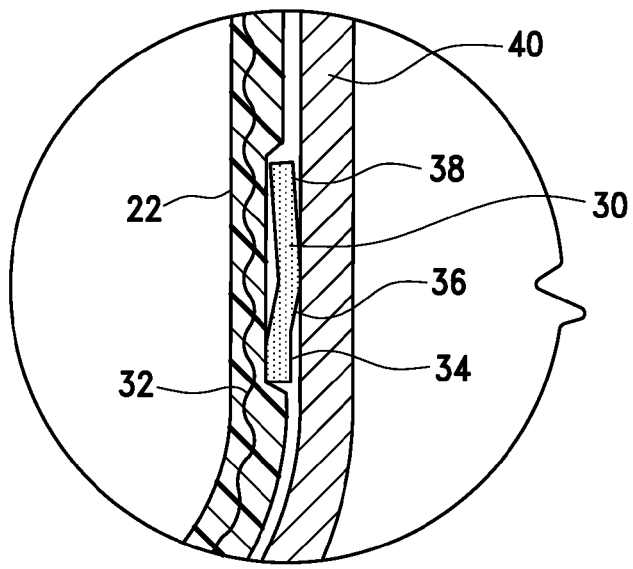
FIG. 20 is a sectional view corresponding to detail I in FIG. 19.
Figure 36:
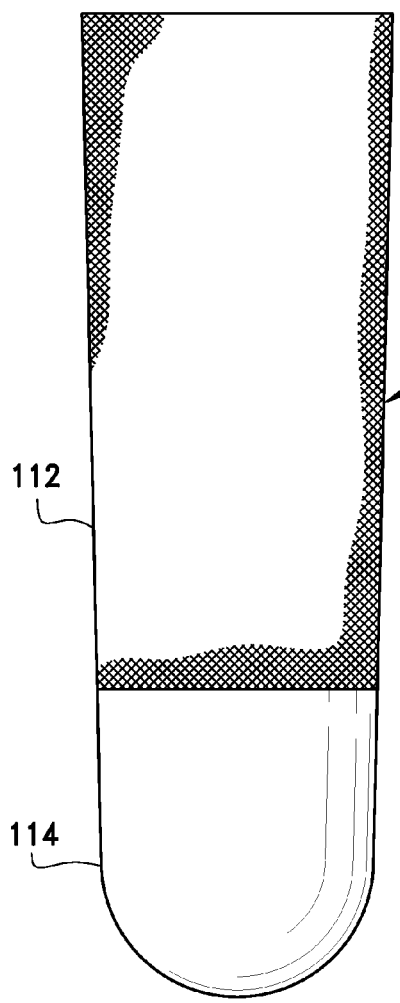
FIG. 36 is an elevational view of another embodiment of a prosthetic liner.

As shown in FIG. 20, the recessed portion 28 may have a depth with a dimension generally corresponding at least to the thickness of the base member 34. Moreover, the length of the recessed portion may be configured so as to have a length that is less than the combined length of the base, outwardly and inwardly members so as to prevent the seal element from becoming completely flat when the sleeve liner is inserted into a hard socket.

With reference to FIGS. 21-35, alternative preferred forms of the seal element shown in FIGS. 17-20 are illustrated. The alternative seal elements may be positioned within the recessed portion of the liner sleeve body portion or along the exterior of the liner sleeve body portion.

As shown by example in FIGS. 21-27, a seal element 42 may have radially pitched members having different lengths, thicknesses and widths, extending at different angles relative to the base member, or may be connected to one another by a connecting member 44 generally parallel with the base member. Moreover, the inwardly pitched member may include at its proximal end an extension member 46 extending generally parallel with the base portion detached from the liner sleeve body portion, or in the alternative, may extend distally beyond the connection to the outwardly pitched member. When extending beyond the outwardly pitched member, such distal portion 48 of the inwardly pitched member may have a curved, straight, or a combination of curved and straight profiles. Similarly, the outwardly pitched member may also extend proximally beyond the connection to the inwardly pitched member and such proximal portion 50 thereof may have a curved, straight, or a combination of curved and straight profiles.

In another configuration of the seal element of the invention illustrated in FIGS. 28-30, the radially outwardly and inwardly pitched members may be replaced by a curved member 52 that extends from the base member of the seal element. Said curved member may be defined as extending outwardly from the liner sleeve body portion to an apex and then extending inwardly towards the liner sleeve body portion a predetermined distance. The inwardly extending portion of the curved member may extend a distance from the apex short of the outer periphery of the liner sleeve body portion. Moreover, the curved member may include at its proximal end an extension member 54 that is detached from the liner sleeve body portion and substantially parallel with the base portion.

In yet another configuration of the seal element of the invention illustrated in FIGS. 31-35, the seal element may include a tapered segment 56 that extends proximally from the base member and under an outwardly pitched member or curved member. Furthermore, in the event the inwardly pitched member or the proximal end of the curved member is connected to an extension member 46 extending proximally therefrom, the extension member 46 may also include a tapered portion 56 distally extending under an inwardly pitched member or curved member of the seal element.

In another embodiment shown in FIGS. 36-40, a liner sleeve 110 is provided which includes two main sections, proximal section 112, and distal section 114. The proximal section 112 comprises a textile having an inner surface that is coated with a silicone composition. The distal section 114 comprises an outer surface that is a silicone composition.

According to one variation, the distal section consists of a silicone composition. In another variation, the distal section comprises a textile that is coated on both its inner and outer surfaces with a silicone composition. The outer surface of the distal section may be substantially smooth, and may have an inherent tackiness.

As with other liner sleeve embodiments described herein, the liner sleeve 110 may include a reinforcement material that is associated with the liner sleeve and located over a length at least coinciding with the location of a sealing member 116 when fitted onto the liner sleeve 110.

Figure 37:
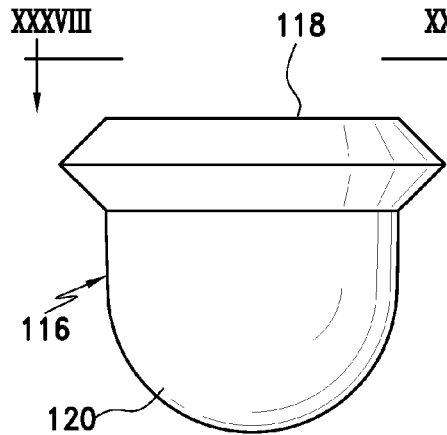
FIG. 37 is an elevational view of an embodiment of an embodiment of a sealing member.
Figure 38:
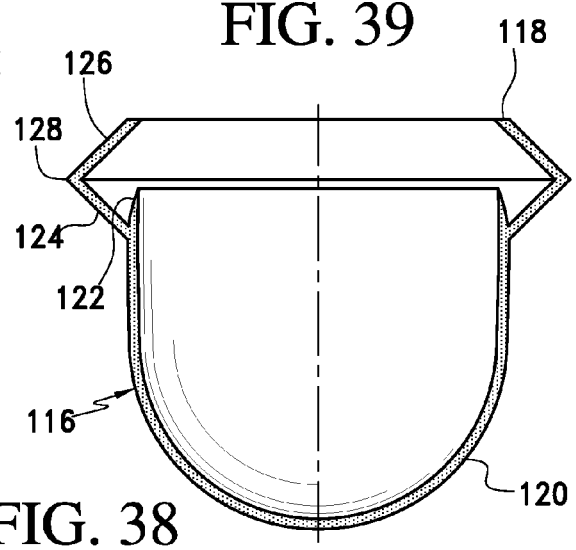
FIG. 38 is a sectional view taken along line XXXVIII-XXXVIII in FIG. 37.

Turning to FIGS. 37 and 38, the sealing member 116 is provided that is separate from the liner sleeve 110. The sealing member 116 includes a seal element 118 provided at a proximal end area of the sealing member 116. The sealing member 116 also includes a receiving portion 120 located at the distal end area of the sealing member 116.

According to FIGS. 37 and 38, the seal element 118 may have inwardly pitched members 124, 126 which meet at peak 128 which forms a radially extending annular ring about the sealing member 116. The seal element 118 may have any configuration shown in FIGS. 17-35.

As with the embodiment in FIG. 31, the seal element 118 of the sealing member 116 may include a lip 122 extending from the receiving portion towards the proximal end of the sealing member 116. According to this variation, the lip 122 is adapted to extend generally parallel to the outer wall of the liner sleeve 110.

The receiving portion 120 of the sealing member 116 is adapted to correspond to the shape of the distal end area of the liner sleeve 110. As shown in FIGS. 37-38, the receiving portion 120 is generally cup-shaped and spherical in nature, and the seal element 118 extends radially outwardly relative to the outer wall of the receiving portion 120. The receiving portion is not limited to a cup-shaped configuration and any suitable configuration that will correspond to a distal end area of a liner sleeve may be used.

The sealing member 116 may be constructed from a variety of materials, such as polymers, rubbers, coated textiles and any other suitable material. According to the embodiment of FIGS. 36-39, the sealing member 116 is constructed from a silicone composition such that along with the silicone outer surface of the liner sleeve 110, the sealing member 116 and the liner sleeve 110 will frictionally fit with one another due to their inherent tackiness when they are contiguous. Moreover, as the sealing member 116 is fitted onto the distal end area of the liner sleeve, air is expelled so as to enable the sealing member 116 to remain on the distal end area of the liner sleeve 110, and form an air-tight seal at portions corresponding to the receiving portion 120. The lip 122 serves to divide the air-tight seal of the receiving portion 120 from the seal element 116, so the seal element 116 can form an air-tight seal between the hard socket 132 and the liner sleeve 110.

Figure 39:
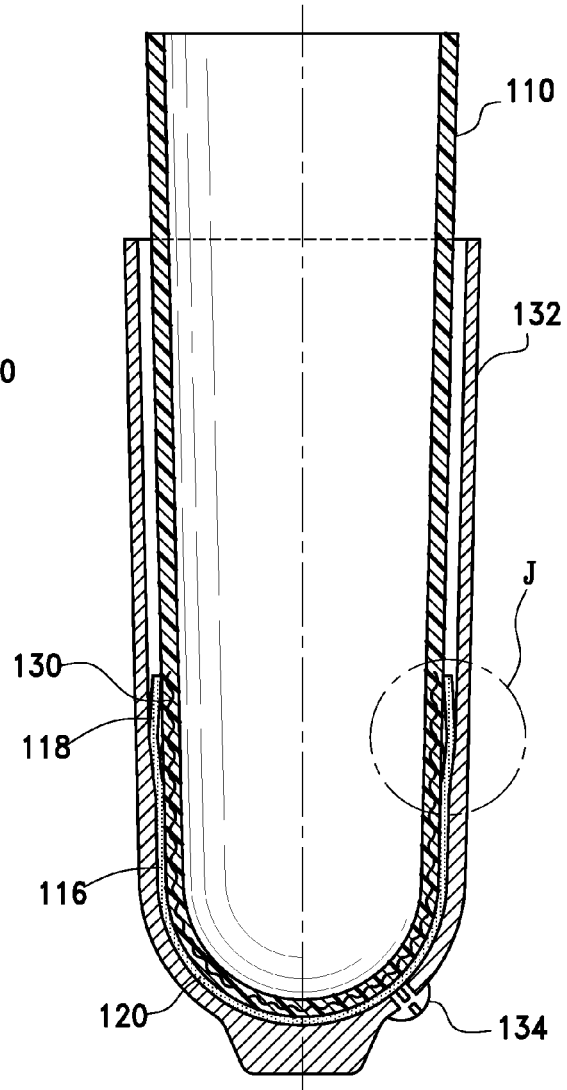
FIG. 39 is a vertical sectional view of an alternate prosthesis system including the liner sleeve of FIG. 36.
Figure 40:
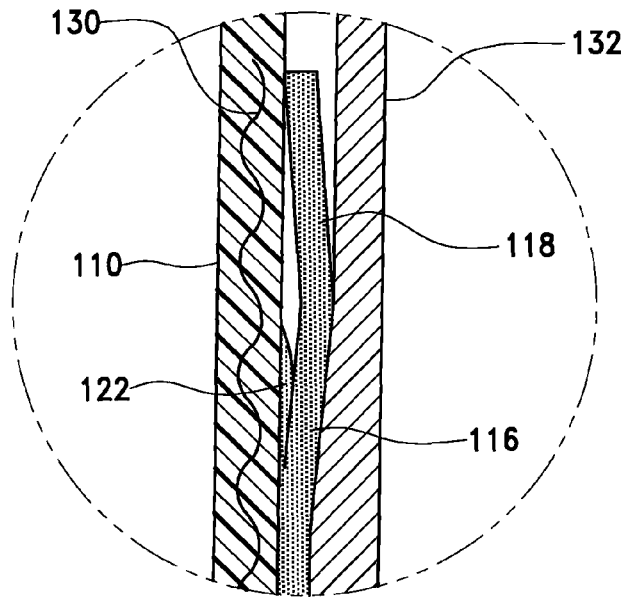
FIG. 40 is a sectional view corresponding to detail J in FIG. 39.

As shown in FIGS. 39 and 40, the liner sleeve 110 and the sealing member 116 form part of a prosthesis system that further includes the hard socket 132 having a one-way distal valve 134. Just as discussed above in reference to other embodiments, the combination of the liner sleeve 110 and sealing member 116 conform to the shape of the internal socket wall, providing an airtight seal. When the liner sleeve 110 is fitted with the sealing member 116, and fitted in the socket, air is expelled through the distal valve 134, thereby creating hypobaric suction below the seal. The reinforcement material 130 of the liner sleeve 110 is provided to prevent elongation of tissue of the residual limb fitted with the socket.

Figure 41:
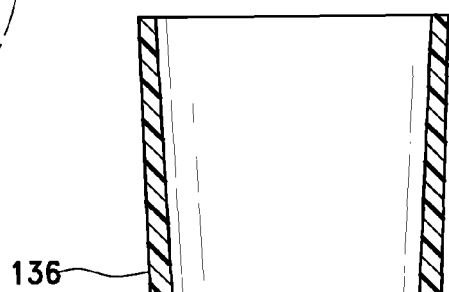
FIG. 41 is a vertical sectional view of an alternate sealing member and prosthetic liner.
Figure 42:
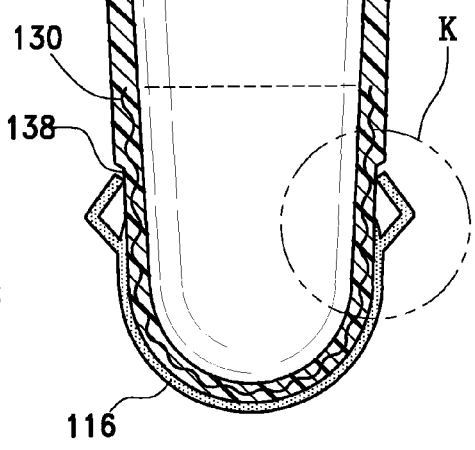
FIG. 42 is a sectional view corresponding to detail K in FIG. 41.

In another embodiment shown in FIGS. 41 and 42, the liner sleeve 136 includes a recessed portion 138 that extends from a distal area of the liner sleeve to the distal end of the liner sleeve. The extent of the recessed portion 138 is governed by the size of the sealing member 116 so that the seal element can be deflected into the recessed portion 138, and so that the receiving portion 120 forms an air-tight seal over the recessed portion 138 below the region in which the seal element 118 may be deflected. The recessed portion 138 is reinforced with reinforcement material 130 as in other embodiments described herein. In variations of this embodiment, the recessed portion 138 may merely comprise an annular recess that does not form the entirety of the distal end area. An example of such a recessed portion may be found in the embodiment of FIG. 17.

Figure 43:
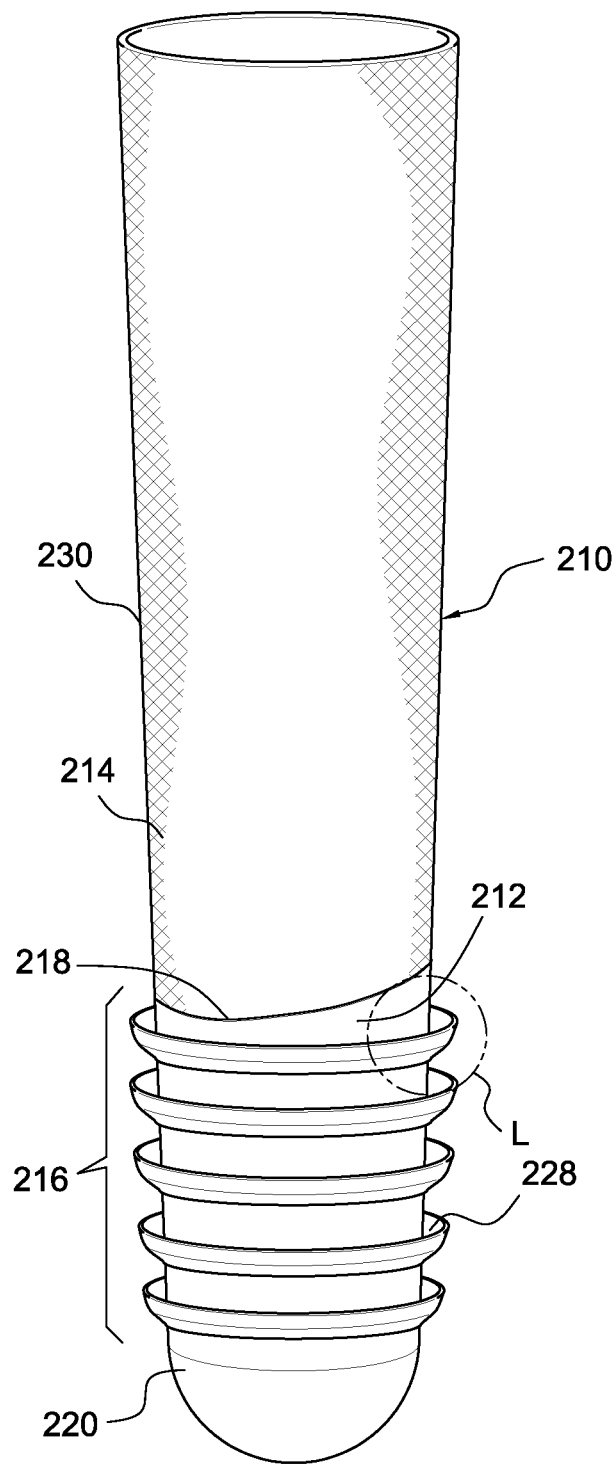
FIG. 43 is an elevational view of another embodiment of a prosthetic liner.
Figure 44:
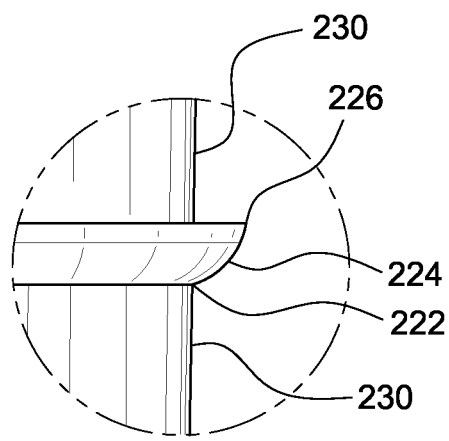
FIG. 44 is a sectional view corresponding to detail L in FIG. 43.

In accordance with another embodiment exemplified by FIGS. 43 and 44, a liner sleeve 210 includes an elongate, generally conical body portion formed from first and second material segments 212, 214 that are at least radially elastically extensible from a relaxed non-extended condition and including proximal and distal end areas. The first material segment 212 may have stiffness greater than the stiffness of the second material segment 214. The liner sleeve 210 defines a continuous profile 230 extending between the distal and proximal end areas. A distal reinforcing cup or umbrella 220 is provided at the distal end of the liner 210.

The first and second material segments may be matrix material or reinforcing material, or a covering material described directly herein, described by way of the incorporated references, or known to those skilled in the art of liner sleeves.

The first and second material segments 212, 214 are secured to one another along a seam 218. The seam 218 may have a variety of shapes, and may be configured to provide a gradual change relative to the distal and proximal end areas, as depicted in FIG. 43. The gradual change of the seam 218 may result in change in stiffness about the periphery of the liner sleeve by virtue of the different degrees of stiffness of the first and second material segments. Thus, by way of example, if the liner sleeve 210 is worn on a residual limb, the anterior side of the liner sleeve may have less overall stiffness than the posterior side due to the seam on the anterior side being located closer to the distal end area of the liner sleeve.

As with other embodiments described herein, a layer of a polymeric material, such as silicone, is provided on an inner surface of the second matrix material. As such, the polymeric layer defines the inner surface of the liner sleeve 210 whereas the second material segment may define the outer surface of the liner sleeve 210.

The polymeric layer may impregnate the first material segment 212 so that the polymeric layer continuously defines the entirety of the inner surface of the liner sleeve. When the first material segment is impregnated within the polymeric layer, the outer surface of the liner sleeve at the region corresponding to the first material segment may be defined by the polymeric layer, as in the embodiment of FIGS. 1-3. In variations, the liner sleeve may be constructed in accordance with any of the embodiments described herein.

The liner sleeve 210 includes a plurality of resilient seal elements 216 protruding radially from the liner body portion along the first material segment 212. The plurality of seal elements 216 may extend either partially or entirely around an outer peripheral portion of the first material segment 212.

Each of the seals 216 includes a root 222 extending from the liner profile 230. An arcuate section 224 projects from the root 222 and terminates at a peak 226. A variable clearance 228 is defined between the arcuate or curvilinear section 224 and the liner profile 230. The seal 216 is arranged for deflection towards the liner profile 230 of the liner sleeve 210 when donned on a residual limb and placed within a prosthetic socket.

The plurality of seals 216 may be formed in accordance with any of the embodiments described herein. For example, they may be formed separately from the liner sleeve and secured thereto by suitable methods. Alternatively, the seals may be formed integrally with or molded from the polymeric layer. Further, the profile of the seals is not limited to arcuate or curvilinear forms, but may be substantially linear or comprised of multiple linear segments.

In accordance with another embodiment exemplified by FIGS. 45-47 and similar to the embodiment of FIGS. 43 and 44, a liner sleeve 310 includes an elongate, generally conical body portion formed from first and second material segments 312, 314 that is at least radially elastically extensible from a relaxed non-extended condition and including proximal and distal end areas. The first and second material segments 312, 314 are secured to one another along a seam 326. The liner sleeve 310 defines a continuous profile 324 extending between the distal and proximal end areas. A distal reinforcing cup or umbrella 313 is provided at the distal end of the liner sleeve 310. The construction of the first and second material segments 312 and 314 may constructed similarly to those of FIGS. 43 and 44.

Unlike the embodiment of FIGS. 43 and 44, the first and second material segments 312, 314 both define the outer surface of the liner sleeve 310.

The liner sleeve 310 includes a plurality of resilient seal elements 316 protruding radially from the first material segment 312 and beyond the liner profile 324. The plurality of seal elements 316 may extend either partially or entirely around an outer peripheral portion of the first material segment 212.

Each of the seals 316 includes a distal root 318 extending from the liner profile 320. A distal arcuate section 320 projects from the distal root 318 and terminates at a peak 322. A proximal arcuate section 321 extends from the peak 322 to a proximal root 319. The seals 316 are arranged for deflection towards the liner profile 324 of the liner sleeve 310 when donned on a residual limb and placed within a prosthetic socket.

A recess 330 is generally formed at both the distal and proximal roots 318, 319. The recess 330 decreases friction at the roots 318, 319, against a hard, definitive socket when the liner 310 is worn in combination with the hard socket. The recess 330 provides a peel-off effect when the liner is removed from the socket, wherein the recesses may allow for a pistoning effect to break the seal of the liner against the socket.

It follows that the recess eliminates or minimizes shear forces existent between the socket and the liner, especially removal. Through these attributes of the recesses, the recesses improve the durability of the seals and thus the liner by reducing wear on the seals themselves decreasing pressure points at the seal roots.

FIG. 47 specifically exemplifies the construction of the liner sleeve 310 along the first material segment 312. The liner sleeve 310 may have a dual polymeric or silicone layer construction, such as different silicone layers 324, 326, as taught in U.S. Pat. No. 6,136,039, owned by the assignee of this disclosure and incorporated herein by reference. The silicone layers 324, 326, each have a different hardness, wherein the outer layer 326 is harder than the inner layer 324. The first material segment 312 is generally adhered to the outer layer 326. At areas of the seals 316, a portion of the silicone of the outer layer 326 extends through the first material segment 312.

The liner sleeve 310 of the embodiment of FIG. 45-47 may be constructed in accordance with the following method. First, the first and second material segments are sewn together along a common seam. The distal reinforcing cup is then molded onto the first material segment. The sewn together first and second material segments are placed into a liner mold, much in a same manner and using similar matrix materials as taught in U.S. Pat. No. 6,485,776, commonly owned by the assignee of this disclosure and incorporated herein by reference. Unlike U.S. Pat. No. 6,485,776, however, the liner mold includes a plurality of small annular grooves corresponding to the plurality of seals 316.

As in U.S. Pat. No. 6,136,039, two types of silicone are injected into the mold, with the first silicone having a higher hardness when cured than the second silicone. Because the grooves in the molds are relatively small, and the pressure in the mold is relatively high, the first silicone is squeezed through first material segment into the grooves of the mold. It will be noted that whereas the first material segment is generally stiffer in nature than the second material segment, the first material segment is selected on the basis that it does not stretch into the grooves of the mold, thereby allowing only the first silicone to pass through the first material segment to form the plurality of seals.

The liner sleeve of any of the embodiments herein may be constructed in the manner described above in reference to the embodiment of FIGS. 45-47. Moreover, the liner sleeve is not limited to having two layers of silicone each having a different hardness, but may comprise a single silicone layer or multiple layers of silicone beyond just the two described herein.

The liner sleeve is not limited to being formed at least in part from silicone. Other suitable polymeric materials for use in liner sleeves may used, as explained in greater detail in U.S. Pat. Nos. 6,706,364 and 6,964,688, both of which are incorporated herein by reference.

The embodiments of the liner sleeve described herein are not limited to being formed with corresponding matrix materials. Instead, they may be made without any matrix materials, and solely with molded polymeric materials. Additionally, a liner sleeve may be provided with at least one covering or segments thereof which cover the outer portion of the polymeric portions of the liner sleeve but do not necessarily serve as a reinforcing material.

The embodiments of FIGS. 43-47 are advantageous in that they do not strangle a residual limb on trans-tibial users since the plurality of seals more evenly distribute traction than a single seal system. It follows that by providing multiple seals, the seal does not create localized pressure peaks on the residual limb. The strangling of residual limbs may occur at bony or sensitive areas of the residual limb. Moreover, by virtue of the method for making liner of FIGS. 45-47, there is no need to adhere a seal to the liner which greatly simplifies the manufacturing and improves the durability of the liner.

It will be understood that the aforementioned embodiments of the present invention are not limited to the described combination of the liner sleeve body portion, seal element and hard socket. Instead, the features of one of the preferred embodiments of the present invention may readily be combined with those of another or other embodiments of the present invention without departing from the scope of the present invention.

It will be readily understood that the described embodiments of the invention are exemplary only and various other features and details could be incorporated in the system described herein without departing from the spirit and scope of the invention as defined in the appended claims.

The invention claimed is:

1. A combination of a suspension liner and a sealing member, the sealing member including a receiving portion, and outwardly and inwardly pitched members extending from the receiving portion and defining a first peak from opposing directions to form a radially extending annular ring, the sealing member being repeatedly installable onto and removable from the suspension liner, and the sealing member being arranged so air is arranged to be expelled as the sealing member is installed onto the suspension liner;

wherein the sealing member has an inherent tackiness and is arranged to frictionally fit against an outer surface of the suspension liner due to the inherent tackiness when at least the receiving portion is contiguous to the outer surface of the suspension liner, the sealing member forming an air-tight seal against the suspension liner at portions corresponding to the receiving portion such that air is expelled from between the suspension liner and the sealing member so as to enable the sealing member to remain secured to the outer surface of the suspension liner.

2. The combination of claim 1, wherein the sealing member defines a lip extending from the receiving portion towards a proximal end of the sealing member.

3. The combination of claim 2, wherein the lip is adapted to extend parallel to the outer surface of the suspension liner.

4. The combination of claim 1, wherein the outwardly pitched. member extends proximally beyond a connection to the inwardly pitched member.

5. The combination of claim 4, wherein each of the inwardly pitched member and the outwardly pitched member have a linear profile.

6. The combination of claim 1, wherein said first peak is arranged to collapse toward the outer surface of the suspension liner.

7. A prosthetic system, comprising:
a flexible suspension liner;
a flexible sealing member including a receiving portion, and outwardly and inwardly pitched members extending from the receiving portion and defining a first peak from opposing directions to form a radially extending annular ring, the sealing member being repeatedly installable onto and removable from the suspension liner, and the sealing member being arranged so air is arranged to be expelled as the sealing member is installed onto the suspension liner;
a hard socket defining an interior wall and including a one-way valve;
wherein the suspension liner and the sealing member are adapted to be placed into the hard socket, the sealing member generally conforming to the shape of the hard socket and providing an air-tight seal therebetween, such that air is expelled through the one-way valve and hypobaric suction is created below the sealing member.

8. The prosthetic system of claim 7, wherein the sealing member has an inherent tackiness and is arranged to frictionally fit against an outer surface of the suspension liner due to the inherent tackiness when at least the receiving portion is contiguous to the outer surface of the suspension liner, the sealing member forming an air-light seal against the suspension liner at portions corresponding to the receiving portion such that air is expelled from between the suspension liner and the sealing member so as to enable the sealing member to remain secured to the outer surface of the suspension liner.

* * * * *